United States Patent
Breininger et al.

(10) Patent No.: US 11,382,577 B2
(45) Date of Patent: Jul. 12, 2022

(54) DETERMINING STIFFNESS INFORMATION OF A MEDICAL INSTRUMENT

(71) Applicants: Katharina Breininger, Erlangen (DE); Marcus Pfister, Bubenreuth (DE)

(72) Inventors: Katharina Breininger, Erlangen (DE); Marcus Pfister, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 1137 days.

(21) Appl. No.: 15/942,992

(22) Filed: Apr. 2, 2018

(65) Prior Publication Data
US 2018/0279974 A1    Oct. 4, 2018

(30) Foreign Application Priority Data
Apr. 3, 2017   (EP) ..................... 17164593

(51) Int. Cl.
*A61B 6/12*     (2006.01)
*A61B 6/00*     (2006.01)
(Continued)

(52) U.S. Cl.
CPC .................. *A61B 6/12* (2013.01); *A61B 6/03* (2013.01); *A61B 6/463* (2013.01); *A61B 6/487* (2013.01); *A61B 6/504* (2013.01); *A61B 6/5235* (2013.01); *A61B 6/4441* (2013.01); *A61B 6/481* (2013.01); *A61B 6/5223* (2013.01); *G06T 7/30* (2017.01); *G06T 2207/10081* (2013.01); *G06T 2207/30101* (2013.01)

(58) Field of Classification Search
CPC .. A61B 6/12; A61B 6/03; A61B 6/463; A61B 6/487; A61B 6/504; A61B 6/5235; A61B 6/4441; A61B 6/481; A61B 6/5223; G06T 7/30; G06T 2207/10081; G06T 2207/30101
See application file for complete search history.

(56) References Cited

U.S. PATENT DOCUMENTS 6,148,095 A  *  11/2000  Prause .................... G06T 17/00
                                                              382/131
7,500,784 B2    3/2009  Grebner et al.
(Continued)

FOREIGN PATENT DOCUMENTS

DE   102010012621 A1   9/2011
DE   102011005777 A1   9/2012
(Continued)

OTHER PUBLICATIONS

Ellis, B.: "Novel stent promote healing of vessel wall after implantation", in: Cardiology Today, Jan. 2011, p. 36.
(Continued)

*Primary Examiner* — Catherine B Kuhlman
*Assistant Examiner* — Sean A Frith
(74) *Attorney, Agent, or Firm* — Lempia Summerfield Katz LLC

(57) ABSTRACT

Methods and systems are provided for determining a stiffness information of a medical instrument used during a minimally invasive interventional procedure in a vascular system of a patient by recording a three-dimensional volume image of the vascular system at least in the intervention region.

20 Claims, 8 Drawing Sheets

(51) Int. Cl.
*A61B 6/03* (2006.01)
*G06T 7/30* (2017.01)

(56) References Cited

U.S. PATENT DOCUMENTS

| | | | |
|---|---|---|---|
| 9,256,940 B2* | 2/2016 | Carelsen | G06T 7/0012 |
| 9,361,413 B1* | 6/2016 | Bout | G06F 30/23 |
| 2011/0235876 A1 | 9/2011 | Pfister et al. | |
| 2012/0059253 A1* | 3/2012 | Wang | A61B 8/12 |
| | | | 600/427 |
| 2012/0071752 A1* | 3/2012 | Sewell | A61B 34/74 |
| | | | 600/424 |
| 2012/0238871 A1 | 9/2012 | Pfister | |
| 2014/0276038 A1 | 9/2014 | Burnett et al. | |
| 2015/0094567 A1* | 4/2015 | Pfister | A61B 6/463 |
| | | | 600/424 |
| 2015/0104085 A1* | 4/2015 | Schilling | A61B 6/463 |
| | | | 382/128 |
| 2016/0302869 A1* | 10/2016 | Chopra | A61B 1/267 |
| 2016/0307304 A1* | 10/2016 | Sakaguchi | G06T 5/008 |
| 2017/0057169 A1* | 3/2017 | Grbic | B29C 64/386 |
| 2017/0079719 A1* | 3/2017 | Warner | A61B 5/055 |
| 2017/0270663 A1* | 9/2017 | Hoffmann | G06T 17/20 |
| 2018/0085167 A1* | 3/2018 | Goyal | A61B 5/103 |

FOREIGN PATENT DOCUMENTS

| | | |
|---|---|---|
| DE | 102013219737 A1 | 4/2015 |
| WO | 2012114224 A1 | 8/2012 |

OTHER PUBLICATIONS

Lessard, Simon, et al. "Automatic detection of selective arterial devices for advanced visualization during abdominal aortic aneurysm endovascular repair." Medical Engineering and Physics 37.10 (2015): 979-986.

European Office Action for European Patent Application No. 17164593.0-1666, dated Oct. 25, 2017.

\* cited by examiner

DETERMINING STIFFNESS INFORMATION OF A MEDICAL INSTRUMENT

CROSS REFERENCE TO RELATED APPLICATIONS

This application claims the benefit of EP 17164593.0, filed on Apr. 3, 2017, which is hereby incorporated by reference in its entirety.

FIELD

Embodiments relate to determining stiffness information of a medical instrument used during a minimally invasive interventional procedure in a vascular system of a patient

BACKGROUND

Imaging devices, for example x-ray devices with a c-arm, may be used to support persons carrying out a minimally invasive medical interventional procedure. Often, projection images of a low dose, e.g. fluoroscopy images, are used to help a clinician track progress of the interventional procedure and/or to help guide a used medical instrument inside the patient, for example, in the vascular system of the patient.

The projection image may be shown overlaid with information on the vascular system, for example, the course of the vessels. The information may be derived from pre-interventional volume images, for example CT images, that are registered to the x-ray device and/or the projection image. Using the additional information, it is not necessary to inject a contrast agent during the intervention to be able to see the vessels.

An example for such an interventional procedure is a fluoroscopy-controlled, interventional repair to abdominal aortic aneurysms. An abdominal aortic aneurysm (AAA) or aneurysma verum aortae abdominalis is a vascular dilatation on the abdominal aorta, a widening of the abdominal aorta below the branching of the renal arteries in the anterior/posterior diameter of over 30 mm. A stent graft may be used for treating this disease. By way of both groins, guide wires, catheters and/or stent delivery devices are inserted into the aorta. One or more stent grafts (e.g., composite vascular stents) are inserted, as shown, for example, in Cardiology Today, January 2011, page 36. The purpose of using the stent grafts is to position the landing zone of the vascular prosthesis as far as possible in the healthy vascular wall area without coinciding with any important vascular branchings/ostea. For example, the branchings of the renal arteries, of the superior mesenteric artery (e.g., arteria mesenterica superior), of the truncus coeliacus, and of the internal iliac artery (e.g., arteria iliaca interna) are to be kept free. A sensitive step is the placement of the "main stent" in the aorta, during which the vascular branchings/ostea mentioned are not to be blocked. Even with relatively simple stents, that, for example, in addition to the aorta, merely encompass the femoral arteries, the final stent often is to be made up of a "main stent" and "part-stents". Thus, for stents for the femoral arteries, the common iliac arteries (e.g., arteriae iliacae communes) are normally "flange-mounted" onto an aortic stent acting as a main stent. In more complex stents, known as fenestrated or branched stents, other part-stents are added as well. Methods for supporting the interventional procedures using anatomically correct overlaying of, for example, presegmented CT data show the physician the aorta and branching vessels in the form of a permanent roadmap, as described, for example, in DE 10 2011 005 777 A1.

If vessel course information or a pre-interventional volume image is used as an anatomical image (reference image) to create an overlaid support image, a problem is that the information overlaid onto the projection image has been acquired at certain point in time when the instrument was not yet introduced into the vascular system. If, however, the medical instruments, that include a certain stiffness, are present in the vascular system, the medical instruments deform the vessels, for example, the ones they extend in. If the anatomical image overlaid onto the projection image does not show this deformation, an inaccuracy or "incongruity" in the overlay is produced, for example an instrument seemingly lying outside of a vessel, resulting in uncertainties in the navigation during a subsequent intervention, in which the overlay serves as an aid to navigation.

In DE 10 2010 012 621 A1, a way of intra-operatively correcting such deformations is disclosed, in which the medical instrument is located or reconstructed from two X-ray projection images. However, using two projection images requires the c-arm to be moved during the interventional procedure.

US 2015/0094567 A1 discloses a method for correcting such deformations using only one projection. An examination method includes capturing a volume data set of the target region with the examination object (the vascular system), registering the volume data set to the c-arm, and extracting information about an assumed course of the examination object in the volume data set inside the target region. The method also includes generating at least one 2D projection image of a medical instrument inserted in the target region, that includes a deviation between overlay and an actually projected instrument. The method includes 2D/3D merging of the at least one 2D projection image and the registered volume data set for generating a 2D overlay image, detecting the instrument inserted in the target region in the 2D overlay image with a first projection matrix, and generating a virtual 2D projection using a virtual projection matrix. The method includes 3D reconstructing the instrument, in which a 3D position of the instrument is determined from the two projections and overlaying the 2D projection image and the virtual 2D projection and distorting at least one part of the 2D projection image such that the current and the assumed course of the vessels are brought into congruence.

US 2015/0094567 A1 proposes that during the approximation of the depth course of the medical instrument, a smoothing interpolation may be used to determine the position of the instrument, that depending on the assumed inflexibility, e.g. stiffness, of the instrument, is a linear, quadratic or more flexible spline interpolation. A stiffness is assumed to estimate a three-dimensional position information of the instrument from the one two-dimensional projection image. As a consequence, the quality of this depth estimation/approximation largely depends on the matching of the estimated stiffness to the actual stiffness of the medical instrument. However, medical instruments cover a wide range of stiffnesses, such that a flexible device with a low stiffness would closer follow the original course of the vessel than a very stiff device, that would straighten the vessel.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide methods, an x-ray device and a computer program for an estimation of a position information describing the course of a medical instrument in a plane not visible in a single two-dimensional projection image.

In an embodiment, a method provides for determining a stiffness information of a medical instrument. The method includes recording a three-dimensional volume image of the vascular system at least in the intervention region, deriving from the volume image three-dimensional vessel course information, e.g. including centerlines and/or surface information for at least vessels used by the instrument during the interventional procedure and/or the position of ostia along at least a part of the vessels, and recording a two-dimensional projection image of the instrument using an x-ray device. The x-ray device and/or the projection image are registered to the volume image. A stiffness information of the instrument is determined by evaluation of the projection image using segmentation information determined by segmenting the instrument in the projection image and/or the vessel course information.

This stiffness information may be used in an imaging support method as initially described, where the support image is determined by recording a three-dimensional volume image of the vascular system at least in the intervention region, deriving from the volume image three-dimensional vessel course information, e.g. including centerlines and/or surface information and/or volume information for at least vessels used by the instrument during the interventional procedure and/or the position of ostia along at least a part of the vessels, and recording a two-dimensional projection image of the instrument using an x-ray device, wherein the x-ray device and/or the projection image are registered to the volume image. The stiffness information is determined by evaluation of the projection image, for example, using segmentation information determined by segmenting the instrument in the projection image and/or the vessel course information. The stiffness information and the vessel course information are used to estimate a position information describing the course of the instrument in a dimension along to the projection direction of the projection image. A vessel deformation information is determined for at least for vessels through which the instrument extends from the position information, the vessel deformation information describing deformation of vessels due to the stiffness of the instrument. The vessel deformation information is used to create an anatomical image of the intervention region showing the deformed vessels, and to determine the support image by overlaying the anatomical image and the projection image or an instrument image derived therefrom.

An embodiment provides for obtaining the stiffness information of the medical instrument by evaluating the image information of the projection image. The projection image not only shows properties/characteristics of the instrument that may be derived by segmentation of the instrument in the projection image and that allow assumptions on the instrument's stiffness, but also includes information on how the known course of the vessels is affected by the instrument in the dimensions of the image plane. The properties and effects visible in the image plane of the projection image, e.g. the segmentation information of the medical instrument, are used to estimate the stiffness of the instruments as a stiffness information that is used to estimate the position, e.g. the course, of the instrument in the depth direction, for example, a direction perpendicular to the image plane of the projection image, that therefore does not provide position information in this direction.

The estimation of the course of the instrument in three dimensions and the adaptation of overlaid anatomical images (reference images) to the deformation of the vessels caused by the medical instrument is provided. A person carrying out the minimally invasive interventional procedure is provided with more reliable information, depicting better the real circumstances inside the patient, for example the position of ostea (vascular branchings). The information shown is also consistent, for example, when changing the projection geometry and thus updating the support image. Therefore, a clinician develops more trust in the presented data.

One application is the repair of aortic aneurysms, e.g. the visualization of ostea not to be blocked by the stent graft, as the position in the image plane of the projection image and thus the support image may also be impacted by deformations in the dimension perpendicular to the image plane. Moreover, when performing endovascular aneurysm repair (or endovascular aortic repair) (EVAR) as the interventional procedure, multiple medical instruments may be used, each having different stiffness properties. Embodiment provide for estimating the respective stiffnesses from the respective image information and thus correcting for deformations of the vessels specifically for each instrument used.

Embodiment may also be used in other endovascular procedures, for example exchanging aortic valves, interventions at the coronary arteries among others.

Embodiments may also be applied if multiple instruments are used at the same time, for example a catheter and a guide wire, both having different stiffnesses. Then, each instrument may be analyzed independently, according to the steps laid out above.

The support image may be displayed using a display device, such as a monitor. The person carrying out the interventional procedure may then survey the progress/instrument in real time, providing new projection images are recorded regularly. On movement of the instrument, results relating to the previous projection image may be taken into account when a new support image is to be determined such that calculation time and resources needed are decreased.

The projection images may be low-dose fluoroscopy images to limit the x-ray exposure of the patient. Additionally, the projection image and/or volume image are digital subtraction angiography images, e.g. the volume image, facilitating the segmentation of the vessels. The latter may be realized automatically, semi-automatically or manually.

The x-ray device may include a c-arm with an x-ray source and an x-ray detector mounted at opposing ends. Such devices may be used for imaging support for interventional procedures, as the c-arm may be positioned flexibly. The volume image may also be recorded using such an x-ray device in a CT-like manner, by rotating the c-arm around the intervention region. Registration is at least facilitated or inherently present if the volume image is recorded immediately before the interventional procedure begins. The volume image may be a pre-operative image, for example, a CT image.

The stiffness information, position information and vessel deformation information may be determined automatically by respective computing units.

The vessel course information may be derived from the volume image automatically and/or the segmentation information is derived from the projection image automatically, for example, using a respective segmentation algorithm.

Corresponding methods and algorithms are known from the state of the art. Segmentation information is referred to an article by S. Lessard et al., "Automatic detection of selective arterial devices for advanced visualization during abdominal aortic aneurysm endovascular repair", Med Eng Phys 37(10): 979-986, October 2015.

In an embodiment, the anatomical image may be determined indicating at least one ostium in a position shifted with respect to its position according to the vessel course information due to the deformation of the vessels. The positions of ostia are important in EVAR procedures and may vary in the image plane even if the vessel is deformed out of plane, for example, if the vessel is compressed due to straightening by the instrument. Embodiments provide for better estimates of the deformation in the depth dimension and thus more reliable depiction of the position of ostia. The positions may already be included in the vessel course information, as are either or both of vessel centerlines and vessel surfaces, that is, boundaries. The vessel course information may also include mathematical descriptions of the vessel course, for example by parametrized polynomials, and/or volume information.

If the projection geometry of the projection image is changed to a new projection geometry, in which a new projection image is recorded, where a new anatomical image is determined, the position information is taken into account from the previous projection geometry. The three-dimensional course of the instrument may be estimated more reliably if the projection geometry is changed.

In an embodiment, at least one schematical image depicting the instrument and at least the vessels the instrument extends through in a plane different from, for example, perpendicular to, the image plane of the projection image is determined using the position information and the vessel deformation information. Using the three-dimensional position of the medical instrument and the deformation of the vessels, it is possible to provide an operator carrying out the interventional procedure with schematical views in other projections as further support images, resulting in a better ability to perceive the current situation.

In an embodiment, the stiffness information is determined using at least one comparison information that is determined by comparing the course of the at least one vessel the instrument extends through according to the vessel course information and the course of the instrument according to the segmentation information. As, from the vessel course information, how the not deformed vessel should look like in the projection image is identified and the projected deformed view of the vessel may be derived from the course of the instrument in the vessel, a measure may be determined, describing how much the medical instrument has deformed the vessel in the projected view. The measure is a measure of the stiffness of the instrument, showing in how far the instrument follows the vessel or deforms it, if the instrument is stiffer. In other words, if the medical instrument deviates strongly from the original course of the vessel, the vessel may be very stiff. If, alternatively, the medical instrument tends to more strongly follow the original course of the vessel, the medical instrument may be is flexible, causing less deformation to the vessel.

In an embodiment, at least one distance information describing a distance measure, for example, the Euclidean distance, between the courses and/or at least one length information describing the difference in lengths of the courses and/or at least one curvature information describing the difference between curvatures of the courses may be determined as comparison information. The latter two measures may correspond to an analysis of the first and/or second derivative of the respective courses. Distance measures may be calculated using a given distance function; Euclidian distances may be used.

In an embodiment, the stiffness information is determined using at least one ostium information describing the dislocation of an ostium that is detected in the projection image by image analysis, in respect to the position described in the vessel course information. If the projection image, for example, a DSA image, allows detection of ostia, the position of the ostium as derived from the projection image may be compared to the position according to the vessel course information, resulting in another indication of the stiffness of the medical instrument.

In an embodiment, when determining the stiffness information, at least one characteristic of the instrument is derived from the segmentation information. A classification algorithm and/or a regression algorithm evaluates the at least one characteristic to determine a stiffness class of the instrument. Each stiffness class is assigned a stiffness value used as the stiffness information. Known segmentation algorithms for medical instruments, for example in the above-cited article by S. Lessard et al., deliver properties of the medical instruments as a result, for example the diameter or the presence of markers. The characteristics of the medical instrument may also be used to determine stiffness. Taking into account multiple characteristics and background knowledge on used instruments, a stiffness class of the instrument may be derived from the characteristics. For many applications, a few stiffness classes may suffice, corresponding to the number of different medical instruments typically used. For example, in AAA repair procedures three stiffness classes (or, if only instrument characteristics are used, instrument classes) may for example be defined. In this example, a high diameter instrument without markers may be classified as a delivery device with high stiffness, a low diameter instrument with equidistant markers may be classified as catheter with low stiffness and/or a low diameter instrument without markers may be classified as guide wire with medium stiffness. In an embodiment, a diameter of the instrument and/or a shape of the instrument and/or markers on the instrument may be used as characteristics of the instrument. Other properties of the instrument may also be taken into account.

In an embodiment, the classification algorithm and/or regression algorithm may also evaluate a determined comparison information and/or a determined ostium information to determine the stiffness class. More information apart from instrument characteristics may be added to provide for a better classification and thus determination of the stiffness information.

Embodiments provide that the classification algorithm and/or regression algorithm first determines an estimated instrument class. Additional external information may be used, for example information obtained by scanning a barcode of the instrument before or during the interventional procedure, to verify the instrument class. In medical procedures, used instruments may be unpacked and scanned immediately before use, so that instrument newly appearing in the projection image is one that has been scanned, or, in turn, that any instrument detected may have been scanned before. A plausibility check may be performed. Besides barcode scanning information, other external information may also be used, for example information entered by a user.

If comparison information and/or ostium information are used in the classification process or the process is complicated in another manner, for example when supporting interventional procedures in which a great number of different instruments may be used, an artificial intelligence algorithm trained by machine learning may be used as the classification algorithm and/or regression algorithm. For example, a neural network may be trained by using annotated projection image training data. Machine learning may be used if the correlations between input data and output data become too complex to define results manually.

For determining the position information, a method as described in US 2015/009467 A1 may be used. A projection matrix for a virtual projection is defined by rotating the projection matrix of the projection image by 90 degrees. The virtual 2D projection also shows the depth dimension. In the virtual projection, a course of the instrument may then be defined using the stiffness information. It is, however, also possible to optimize a three-dimensional model, in which the known two-dimensional course of the instrument and the known three-dimensional course of the vessel in a not deformed state are entered. A cost function may be formulated using the stiffness information to find a depth deformation matching the stiffness information determined in the image plane of the projection image.

In an embodiment, the stiffness information includes a relative stiffness parameter selected in an interval between zero and one. The course of the instrument as part of the position information is determined between a non-deformed course of the vessel weighted with one minus the relative stiffness parameter and a maximally straightened, calculated course of the vessel weighted with the relative stiffness parameter, for example, in a projection geometry perpendicular to the projection geometry of the projection image. Two extremes are defined, one relating to a perfectly flexible medical instrument that does not deform the vessel—the course of the vessel described by the vessel course information—and a maximum deformation of the vessel, e.g. completely straightening out curvature, for example, relating to a completely stiff instrument. By weighing the extremes to extremal courses using the stiffness parameter, a simple to realize and qualitatively high depth estimation may be performed. Different types of interpolations between the courses may be used, for example, depending on the stiffness parameter, as described in US 2015/009467 A1, for example a linear, quadratic or spline interpolation.

An embodiment includes an x-ray device, including a control device configured to execute a method as described above. The x-ray device may be a c-arm x-ray imaging device, such that the x-ray device may also be controlled by the control device to record the volume image, that is configured to control the x-ray device to record the projection image.

The control device may include multiple functional units, such as an acquisition unit to control the x-ray device to record the three-dimensional volume image and/or the projection image, a vessel course information determining unit, a stiffness information determining unit, a position information estimating unit, a vessel deformation information determining unit, an anatomical image creating unit and an overlaying unit. The units or additional units may be configured to perform actions as described above.

A computer program according to an embodiment may be loaded into a computing device, for example, a control device of an x-ray device. The computer program may include program code to execute the steps of a method describe above when the computer program is executed in the computing device. The computer program may be stored on an electronically readable storage medium that includes control information stored thereon, that includes the computer program and is configured such that a method describe above is executed when the storage medium is used in a control device of an x-ray device. The storage medium may be a non-transitory storage medium, such as a CD-ROM.

DETAILED DESCRIPTION

Figure 1:
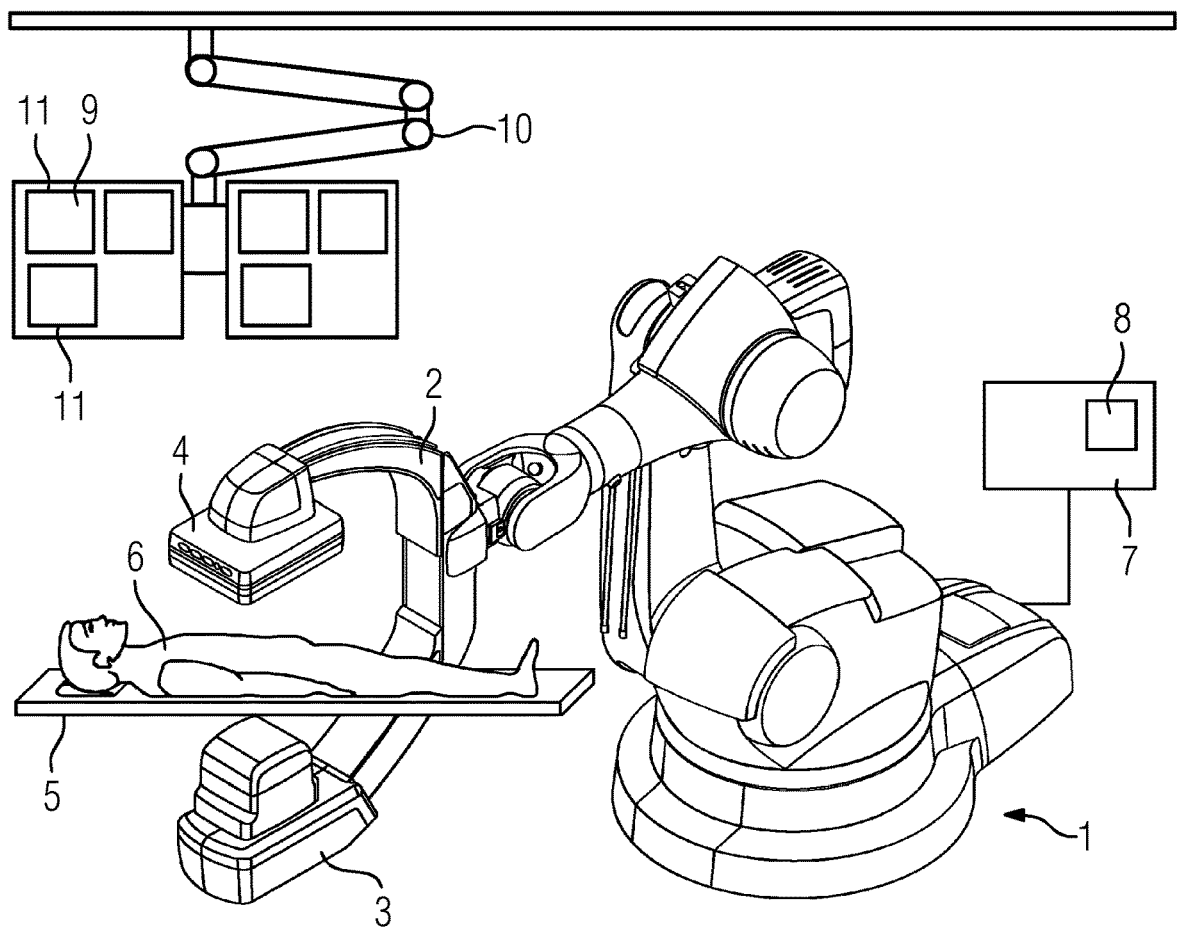
FIG. 1 depicts an x-ray device according to an embodiment.

FIG. 1 depicts a monoplanar x-ray device with a c-arm 2 held by a stand 1 in the form of a six-axis industrial or articulated robot. The x-ray system includes an x-ray source (e.g., an x-ray emitter 3 with x-ray tube and collimator) and an x-ray image detector 4 attached to opposing ends of the c-arm 2.

Using an articulated robot described, for example, in U.S. Pat. No. 7,500,784 B2, that may have six axes of rotation and thus six degrees of freedom, the c-arm 2 may be displaced spatially as required, for example by being rotated about a center of rotation between the x-ray emitter 3 and the X-ray image detector 4. Further degrees of freedom of the angiographic x-ray device 1 may include rotation, for example, about centers of rotation and axes of rotation at the c-arm plane of the x-ray image detector 4 (e.g., about the center of the x-ray image detector 4) and about axes of rotation intersecting the center of the x-ray image detector 4.

Located in the beam path of the x-ray source 3 is a patient 6 to be examined as an examination subject. The patient is positioned on a patient table 5 of a patient positioning device. A control device 7 is connected to an image system 8 that receives and processes the image signals from the x-ray image detector 4. Operating elements of the x-ray device 1 are not depicted. The x-ray images and other images, for example support images, may be viewed on displays 11 of a monitor bracket 9. The monitor bracket 9 may be held by a ceiling-mounted support system 10 with a cantilever arm and a lowerable support arm, may be moved lengthwise, pivot and rotate, and is height-adjustable. The control device 7 is configured to execute a method that is described below.

Figure 2:
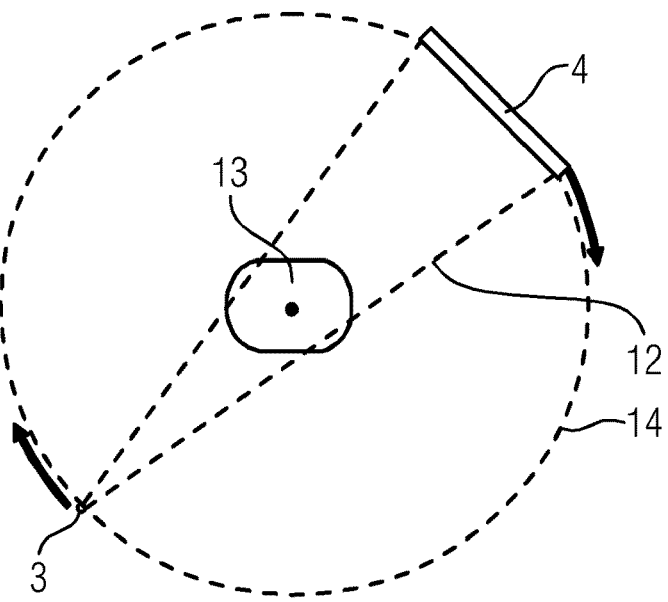
FIG. 2 is an example schematic representation of geometric relationships in rotational angiography using the x-ray device of FIG. 1.

The x-ray source 3 emits a beam of radiation 12 originating from a focal point of the x-ray source 3. The beam is directed to the x-ray image detector 4. If three dimensional volume images are to be generated in accordance with a DynaCT method, a method for rotational angiography, the rotatably mounted c-arm 2 with the x-ray source 3 and the x-ray image detector 4 is rotated such that, as shown schematically in FIG. 2 by the view from above of the axis of rotation, the x-ray source 3 represented by a focal point and the x-ray image detector 4 move in an orbit 14 about an examination region 13 to be examined that is located in the beam path of the x-ray source 3, for example the vascular system of the patient 6 in an intervention region. To generate a three-dimensional volume image, the orbit 14 may be fully or partially used.

In accordance with the DynaCT method, the c-arm 2 with x-ray source 3 and x-ray image detector 4 may be moved over an angular range of at least 180°, for example 180° plus fan beam angle, and records two-dimensional images in rapid succession from various projection geometries along the orbit 14. The reconstruction may be performed using only a part or the whole of this recorded data.

Figure 3:
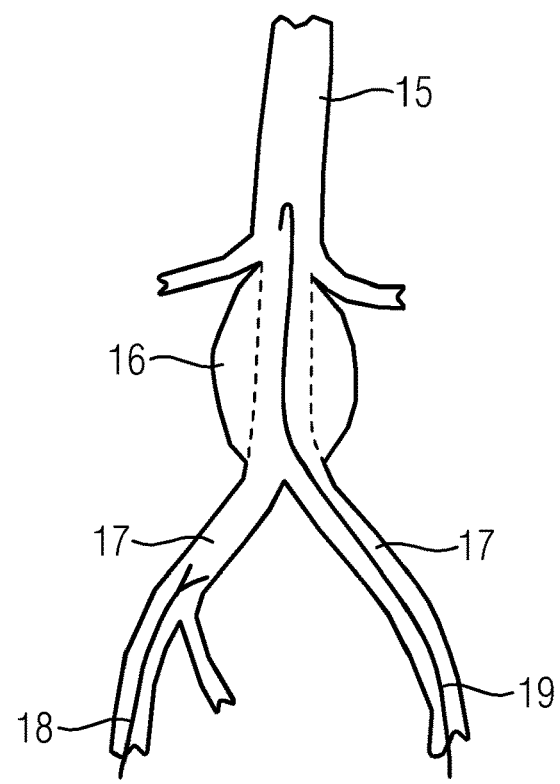
FIG. 3 depicts an abdominal aorta with an aortic aneurysm according to an embodiment.
Figure 4:
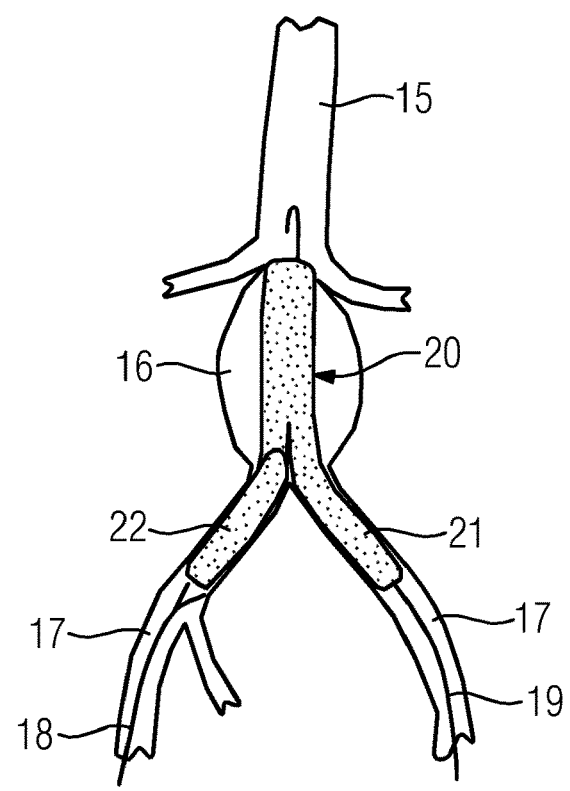
FIG. 4 depicts the aorta of FIG. 3 with an inserted stent graft according to an embodiment.

FIG. 3 depicts an abdominal aorta 15 that includes an abdominal aortic aneurysm (AAA) 16. An AAA 16 is a vascular dilatation on the abdominal aorta 15. The aorta 15 branches into femoral arteries 17. The aortic aneurysm 16 is treated in a minimally invasive interventional procedure by inserting a stent graft, for example, a composite vascular stent, as depicted in FIG. 4. Medical instruments 18, 19, including guide wires, catheters and stent delivery devices, by which stent grafts 20 are delivered to the AAA 16, are inserted into the aorta 15 through the femoral arteries 17 by way of both groins.

In the case of complex stent grafts 20 that also encompass the femoral arteries 17, a final stent may be composed of "part-stents." For example, an iliacal stent 22, as a part-stent for the other femoral artery 17, is to be "flange-mounted" onto an aortic stent 21 as a main stent, that projects through the AAA 16 into one of the femoral arteries 17, through a window.

Figure 5:
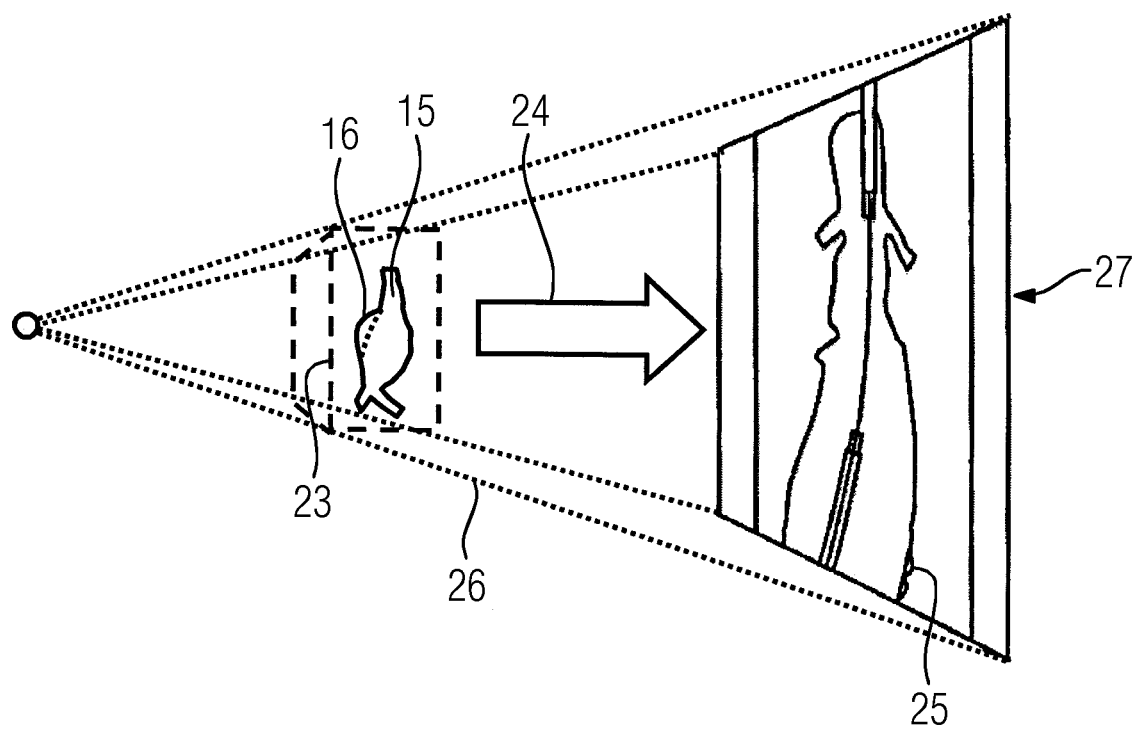
FIG. 5 depicts an example of 2D/3D-overlay.
Figure 6:
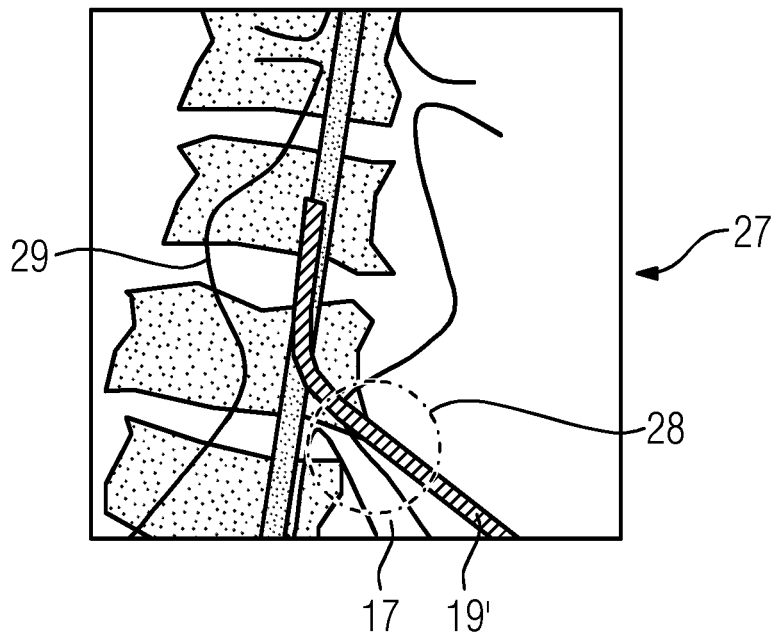
FIG. 6 depicts a support image of an overlay error caused by a deformation of an artery by an inflexible medical instrument.

Using FIGS. 5 and 6, the principle of a 2D/3D is explained in more detail. To provide the physician with additional information as assistance when inserting AAA stents, an anatomical image based on a previously recorded volume image of the vascular system is overlaid anatomically correctly over a current low-dose fluoroscopy projection image generated by the x-ray device 1. The anatomical image may be derived from the volume image. The volume image may be, for example, a preoperative computed tomography or rotational angiography image using the c-arm x-ray device 1.

FIG. 5 depicts an overlay of a current fluoroscopy projection image with the pre-interventionally generated volume image 23. The volume image 23 is mapped by a projection 24 into the image plane of the projection image as anatomical image 25. The forward projection is symbolized by the dotted lines 26. A 2D/3D overlay image is produced as a support image 27. The anatomical image 25 may also be based on a segmentation result of the vascular system, for example vessel course information, for example, corrected using vessel deformation information, as further described below.

FIG. 6 depicts a situation similar to FIG. 3, where a stiff (inflexible) medical instrument 19' is inserted into a vessel, for example, a femoral artery 17. The vessel may in some cases deform to the deformed femoral artery 17'. The level of deformation depends on the actual stiffness of the medical instrument 19'.

Figure 7:
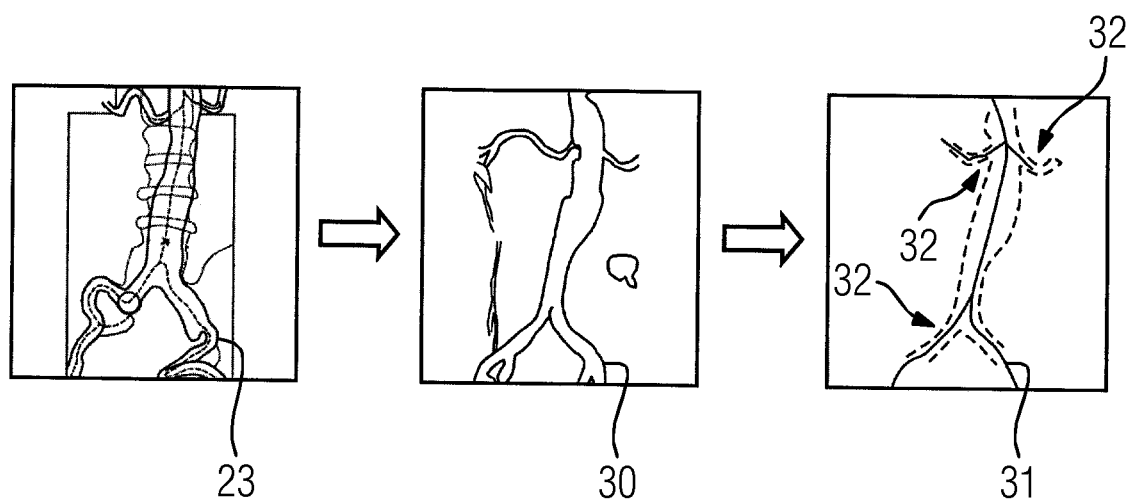
FIG. 7 depicts a segmentation of a volume image.

If this vascular deformation caused by the inflexible medical instrument 19' is not corrected in the corresponding support image 27, an overlay error 28 results, as is schematically depicted in FIG. 7. The instrument 19' lies outside of the vascular system 29, that may lead to uncertainties during the interventional procedure, in which the support image 27 serves as a navigation aid and as a support for surveying progress of the procedure. The overlay error 28 manifests in a virtual deviation of the mapping of the femoral artery 17 from the mapping of the rigid medical instrument 19' in the deformed femoral artery 17'.

Figure 8:
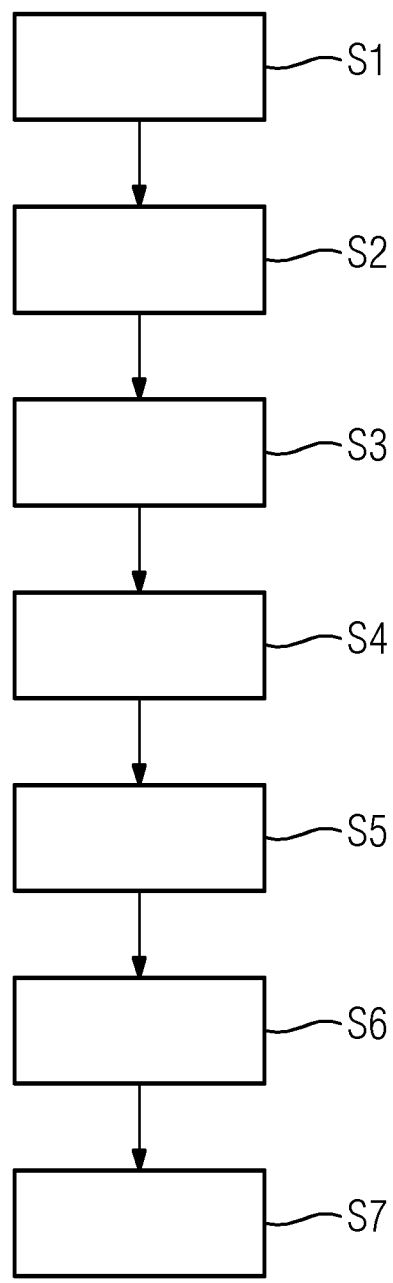
FIG. 8 depicts a flow chart of an embodiment of a method.

According to an embodiment, a vessel course information is determined from the volume image 23 automatically, for example, that is a DSA image, as depicted in FIG. 8. A segmentation algorithm may be used. For example, the surface 30 of the vessels and a course of the vessels may be determined in the form of the centerlines 31 of the vessels. The position of ostea 32 may be determined. The course of the vessels in a model may be mathematically described for example as a higher-grade polynomial.

FIG. 8 depicts a flow chart of a method. At act S1, the three-dimensional volume image 23 is recorded, for example, using the x-ray device 1. At act S2, the vessel course information is determined. The acts may be performed before the interventional procedure and may only need to be performed once, even if multiple projection images are recorded.

At act S3, the two-dimensional projection image showing the instrument 18, 19, 19' in the intervention region is acquired using a projection geometry, and thus projection matrix, that may be automatically and/or manually chosen, using the x-ray device 1.

At act S4, the two-dimensional projection image is evaluated to determine a stiffness information. The medical instrument 18, 19, 19' is segmented in the projection image, using, for example, the algorithms of the cited article by S. Lessard.

Figure 9:
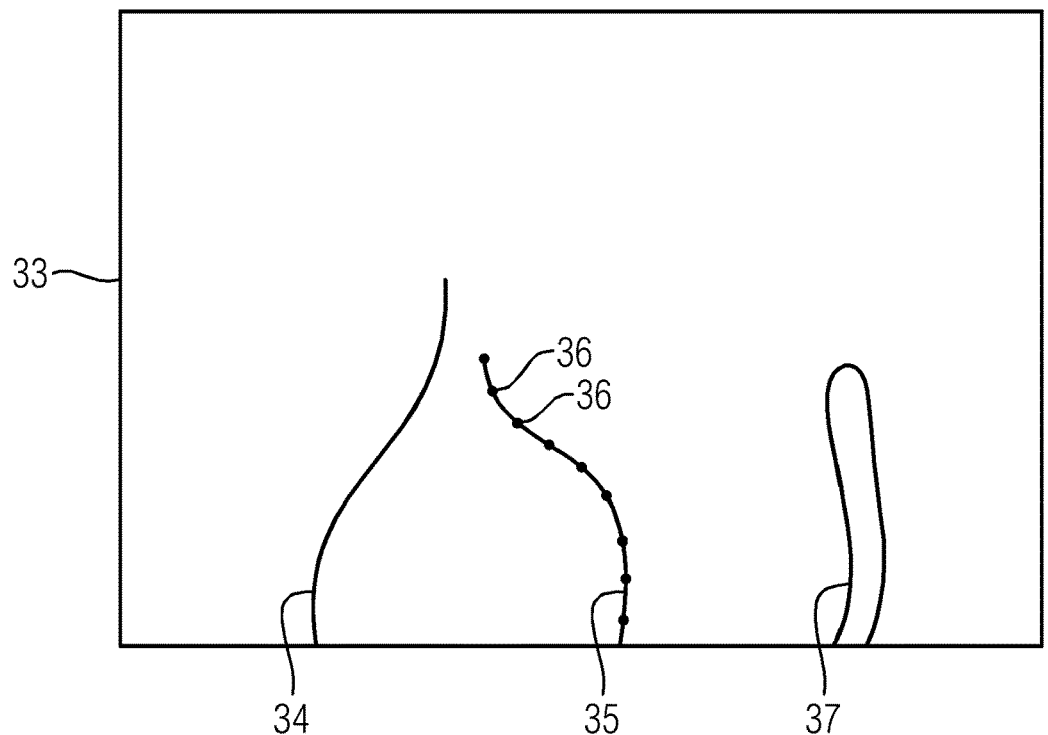
FIG. 9 depicts instruments in a projection image according to an embodiment.

FIG. 9 depicts how different medical instruments 18, 19, 19' appear in a projection image 33. A guide wire 34 has a small diameter and no markers on it. A catheter 35 used in the interventional procedure may have markers 36 or other shape characteristics, while still having a small diameter. A delivery device 37 may have a large diameter. The characteristics may be derived from the segmentation and may include a diameter of the medical instrument 18, 19, 19' and information on markers 36 on the instrument 18, 19, 19'.

Figure 10:
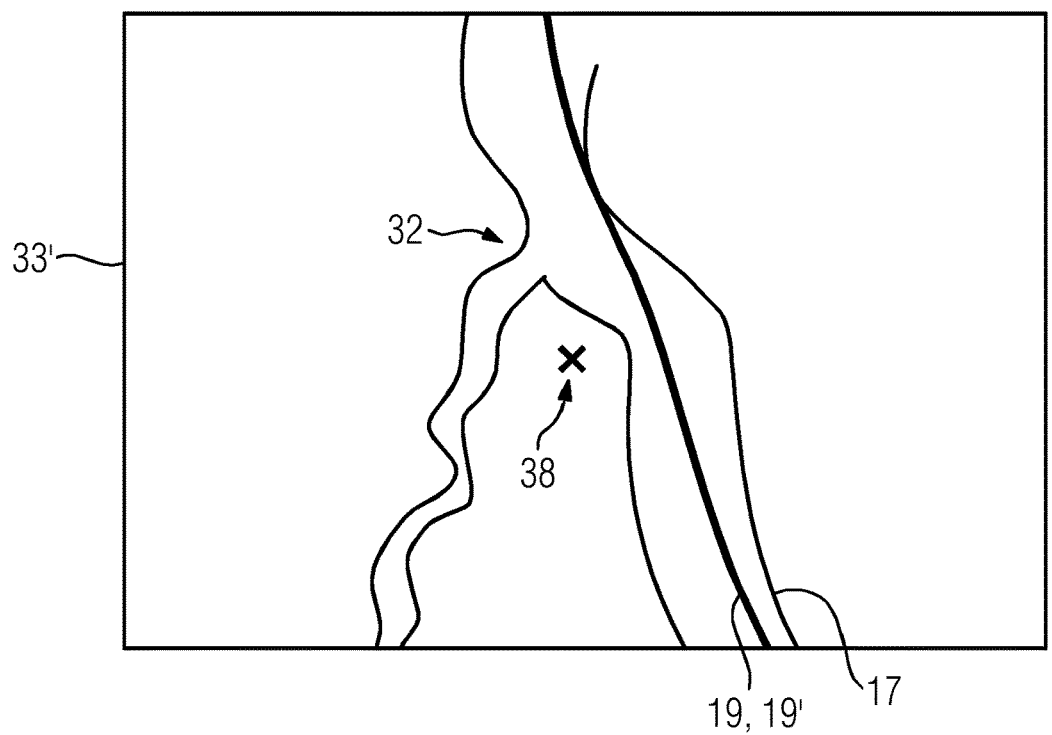
FIG. 10 depicts an example of a DSA projection image.

FIG. 10 depicts another example of a projection image 33', that was recorded as a DSA image. Vessels such as the artery 17 may be seen in the projection image 33', so that a position of an ostium 32 may be determined. The displacement from the position 38 according to the vessel course information may be determined as ostium information.

Figure 11:
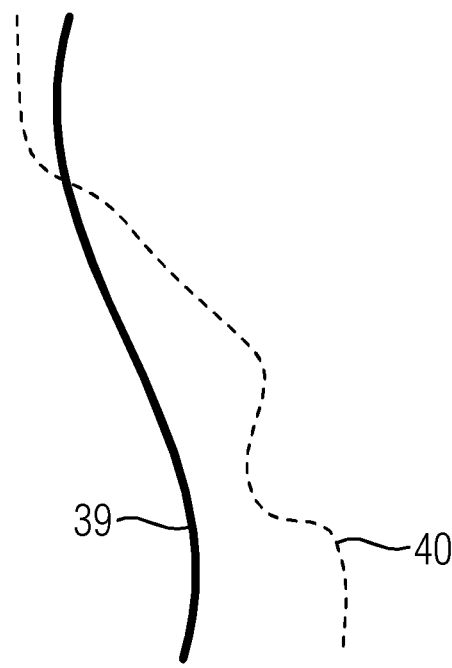
FIG. 11 depicts a determination of a deviation of courses according to an embodiment.

FIG. 11 depicts the determination of a comparison information as a measure of deviation of the course of an instrument 18, 19, 19', illustrated by a centerline 39 and derived from the segmentation, from the course of a vessel through which it extends, illustrated by a centerline 40 of the vessel, according to the vessel course information. Measures for the deviation include a distance information describing the Euclidean distance between the courses, a length information describing the difference in lengths of the courses and a curvature information describing the difference between curvatures of the courses. The comparison information describes the deformation of the vessel in the image plane of the projection image 33, 33' and thus includes information on the stiffness of the medical instrument 18, 19, 19'.

The stiffness information may be determined as a stiffness value, for example, in the interval [0, 1], associated with one of more stiffness classes. To classify the medical instrument 18, 19, 19' into a corresponding stiffness class, a classification algorithm is used, that may also or additionally be a regression algorithm. The classification algorithm may first determine an instrument class of the medical instrument 18, 19, 19' by evaluating the characteristics determined from or in the segmentation information. In the case of repair of an AAA 17, three instrument classes are used, one describing a guide wire 34 (small diameter, no markers, medium stiffness), one a catheter 35 (small diameter, markers, low stiffness) and one a delivery device 37 (high diameter, no markers, high stiffness). If external information on the instruments 18, 19, 19' used is available, the external information may be consulted for verification.

The determinable comparison information may be used to modify or make plausible a result of the instrument classification when stiffness values are associated with the instrument classes as stiffness classes. However, the classification algorithm may, in certain embodiments, also use the comparison information (and, if determinable, ostium information) as input data. In this case and more complex scenarios, such as having way more possible instruments 18, 19, 19', the classification algorithm may also be an artificial intelligence algorithm trained by machine learning.

At act S4, a position information is determined using the stiffness information. The position information describes the course of the medical instrument 19, 19', and thus of the deformed vessel, in three dimensions. Thus, a depth estimation in the dimension perpendicular to the image plane of the projection image 33, 33' is performed.

An optimization algorithm may be used to further distort the vessel course in the dimension to estimate starting from the known 2D distortion with a corresponding cost function. Additionally, the projection matrix approach described in US 2015/0094567 A1 is used to allow calculation of a virtual projection in a direction perpendicular to that of the projection image 33, 33'.

Figure 12:
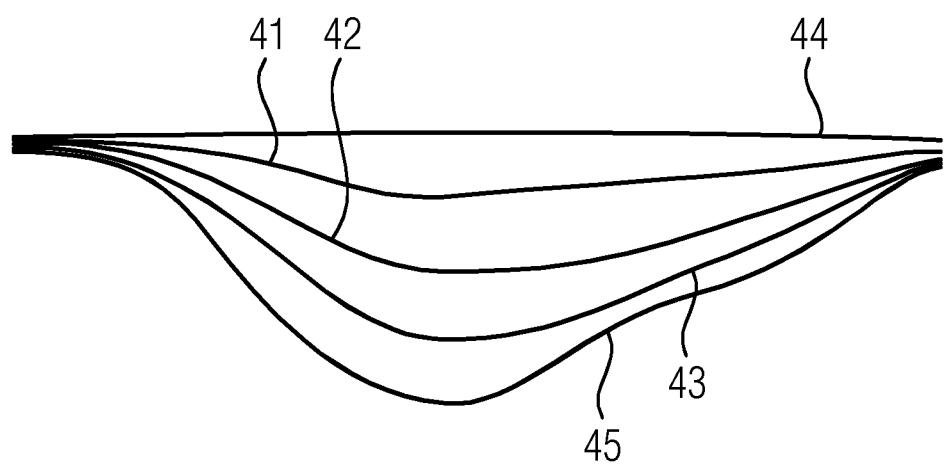
FIG. 12 depicts possible instrument courses according to stiffness.

FIG. 12 depicts possible courses 41, 42, 43 of the medical instrument 18, 19, 19' in such a projection. In the virtual projection, due to the missing depth information, the instrument 18, 19, 19' would first appear straight, e.g. as completely stiff, see extremal course 44. The stiffness information, however, describes in how far the medical instrument 18, 19, 19' will deform the vessel course as a second extremal course 45 in this projection. The stiffness information may be used to weigh each of the extremal courses 44, 45 and interpolate a corresponding course 41, 42, 43. The course 41 corresponds to a high stiffness, for example the delivery device 37, straightening the vessel. The course 42 corresponds to a medium stiffness, for example the guide wire 34, deforming the vessel, but still keeping the original course. The course 45 corresponds to a low stiffness, e.g. high flexibility, for example the catheter 35, only slightly deforming the vessel.

In an embodiment, a relative stiffness parameter chosen in an interval between zero and one is used. The course of the medical instrument 18, 19, 19' as part of the position information is determined between the non-deformed course 45 of the vessel weighted with one minus the relative stiffness parameter and a maximally straightened, calculated course 44 of the vessel weighted with the relative stiffness parameter in the projection geometry perpendicular to the projection geometry of the projection image 33, 33'.

At act S5, a vessel deformation information is derived from the position information. The position information may be used as vessel deformation information, as the course of the medical instrument 18, 19, 19' is inside the vessel. It is also possible to determine the vessel deformation information such that the instrument 18, 19, 19' clings to a vessel wall if the vessel boundaries are described by the vessel course information.

The vessel deformation information provides at act S6 for correction and thus to determine the anatomical image 25 such that the overlay in the support image 27, act S7, shows the deformed vessel with the instrument 18, 19, 19' inside.

Figure 13:
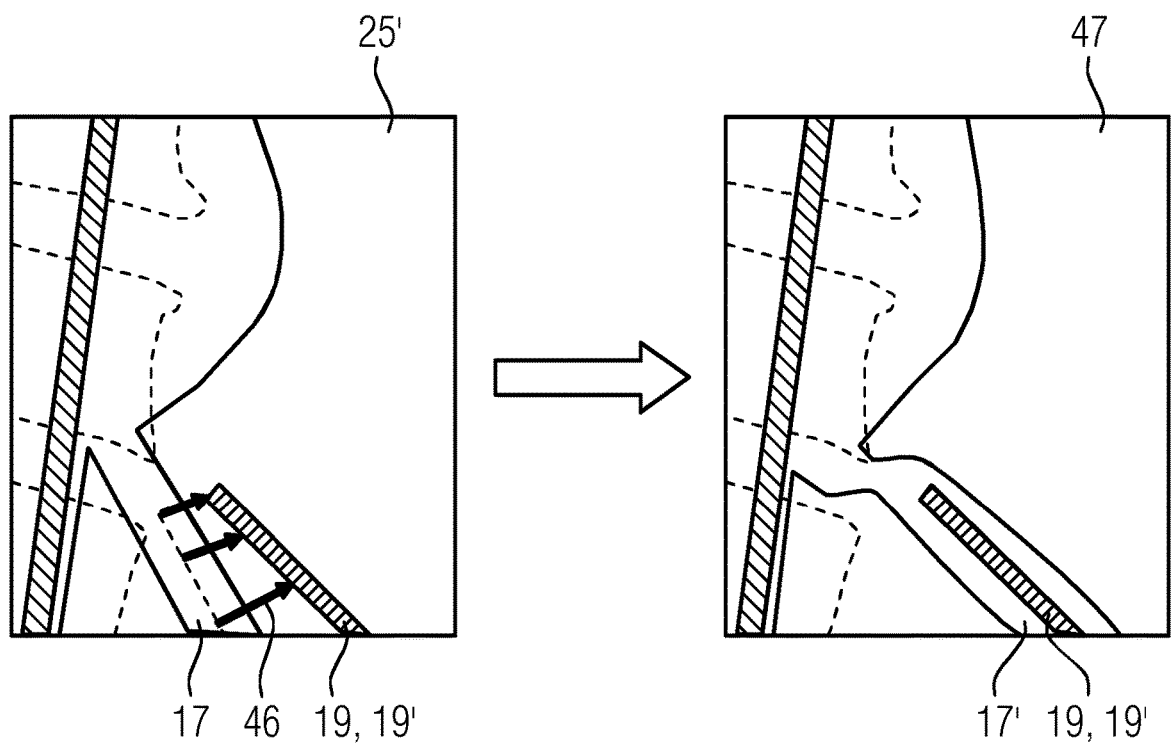
FIG. 13 depicts an example proposed correction in the image plane of the projection image.

The proposed correction is depicted in the image plane based on FIG. 13. An anatomical image 25' that shows the status before the insertion of the medical instrument 19, 19' is overlaid with the actual position and location of the inserted medical instrument 19, 19' indicating the current course of the vessel (e.g., the deformed femoral artery 17'). The anatomical image 25 (e.g., the centerline 31 of the vessel course information) is then distorted according to the displacements 46, so that the current and the assumed course of the deformed femoral artery 17' are again congruent, as is represented in the distorted anatomical image 47.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining stiffness information of a medical instrument used during an interventional procedure in a vascular system of a patient, the method comprising:
    recording a three-dimensional volume image of the vascular system at least in an intervention region;
    deriving three-dimensional vessel course information from the three-dimensional volume image, the three-dimensional vessel course information comprising centerlines for at least vessels used by the medical instrument during the interventional procedure, surface information for at least the vessels used by the medical instrument during the interventional procedure, volume information for at least the vessels used by the medical instrument during the interventional procedure, a position of ostia along at least a part of the vessels, or any combination thereof;
    recording a two-dimensional projection image of the medical instrument using an x-ray device, wherein the x-ray device, the projection image, or the x-ray device and projection image are registered to the three-dimensional volume image; and
    determining the stiffness information of the medical instrument, the determining of the stiffness information comprising evaluating the projection image using segmentation information determined by segmenting the instrument in the projection image, the vessel course information, or the projection image and the vessel course information.

2. The method of claim 1, wherein determining the stiffness information further comprises determining the stiffness information using comparison information that is determined by comparing the course of the at least one vessel the instrument extends through according to the vessel course information and the course of the instrument according to the segmentation information.

3. The method of claim 2, wherein the comparison information comprises distance information describing a distance measure between the courses, length information describing a difference in lengths of the courses, curvature information describing the difference between curvatures of the courses, or any combination thereof.

4. The method of claim 3, wherein the distance measure is an Euclidean distance.

5. The method of claim 1, wherein the stiffness information is determined using at least one ostium information describing the dislocation of an ostium that is detected in the projection image by image analysis with respect to the position described in the vessel course information.

6. The method of claim 1, wherein when determining the stiffness information, at least one characteristic of the instrument is derived from the segmentation information,
wherein a classification algorithm, a regression algorithm, or the classification algorithm and the regression algorithm evaluate the at least one characteristic of the instrument to determine a stiffness class of the instrument, and
wherein each stiffness class is assigned a stiffness value used as the stiffness information.

7. The method of claim 6, wherein the classification algorithm, the regression algorithm, or the classification algorithm and the regression algorithm also evaluate a determined comparison information, a determined ostium information, or the determined comparison information and the determined ostium information to determine the stiffness class.

8. The method of claim 6, wherein the at least one characteristic comprises a diameter of the instrument, a shape of the instrument, or markers on the instrument, or any combination thereof.

9. The method of claim 6, wherein the classification algorithm, the regression algorithm, or the classification algorithm and the regression algorithm determine an estimated instrument class,
wherein additional external information obtained by scanning a barcode of the instrument before or during the interventional procedure is used to verify the instrument class.

10. The method of claim 6, wherein the classification algorithm, the regression algorithm, or the classification algorithm and the regression algorithm are an artificial intelligence algorithm trained by machine learning.

11. A method for imaging support during a minimally invasive interventional procedure using a medical instrument in a vascular system of a patient, in which a support image showing the medical instrument in the vascular system of an intervention region is determined, the method comprising:
determining stiffness information of the instrument by evaluating a projection image using segmentation information determined by segmenting the instrument in the projection image, vessel course information, or the projection image and the vessel course information;
estimating position information describing a course of the medical instrument in a dimension along a projection direction of the projection image using the stiffness information and the course;
determining vessel deformation information at least for vessels through which the medical instrument extends from the position information, the vessel deformation information describing deformation of vessels due to the stiffness of the instrument;
creating an anatomical image of the intervention region showing the deformed vessels using the vessel deformation information; and
determining the support image by overlaying the anatomical image and the projection image or an instrument image derived from the projection image.

12. The method of claim 11, wherein the anatomical image is determined indicating at least one ostium in a position shifted with respect to a position according to the course due to the deformation of the vessels, the projection geometry of the projection image, or the deformation of the vessels and the projection geometry of the projection image is changed to a new projection geometry in which a new projection image is recorded, and
wherein a new anatomical image is determined taking into account the position information from the previous projection geometry, at least one schematical image showing the medical instrument and at least the vessels the instrument extends through in a plane different from the image plane of the projection image, or a combination thereof is determined using the position information and the vessel deformation information.

13. The method of claim 11, wherein the stiffness information comprises a relative stiffness parameter selected in an interval between zero and one, and
wherein the course of the medical instrument as part of the position information is determined between a non-deformed course of the vessel weighted with one minus the relative stiffness parameter and a maximally straightened, calculated course of the vessel weighted with the relative stiffness parameter in a projection geometry perpendicular to the projection geometry of the projection image.

14. A system for determining stiffness information of a medical instrument used during an interventional procedure in a vascular system of a patient, the system comprising:
an X-ray device configured to record a three-dimensional volume image of the vascular system at least in an intervention region, the X-ray device further configured to record a two-dimensional projection image of the medical instrument using an x-ray device, wherein the x-ray device, the projection image, or the x-ray device and projection image are registered to the three-dimensional volume image; and
a control device configured to derive from the three-dimensional volume image, three-dimensional vessel course information, the three-dimensional vessel course information comprising centerlines of at least vessels used by the medical instrument during the interventional procedure, surface information of at least the vessels used by the medical instrument during the interventional procedure, volume information of at least the vessels used by the medical instrument during the interventional procedure, a position of ostia along at least a part of the vessels, or any combination thereof,
wherein the control device is further configured to determine the stiffness information of the medical instrument, the determination of the stiffness information of the medical instrument comprising evaluation of the projection image using segmentation information determined by segmentation of the instrument in the projection image, the vessel course information, or the projection image and the vessel course information.

15. The system of claim 14, wherein the stiffness information is determined using comparison information that is determined by comparison of the course of the at least one vessel the instrument extends through according to the vessel course information and the course of the instrument according to the segmentation information.

16. The system of claim 15, wherein the comparison information comprises distance information describing a distance measure between the courses, length information describing a difference in lengths of the courses, curvature information describing the difference between curvatures of the courses, or any combination thereof.

17. The system of claim 14, wherein the stiffness information is determined using ostium information describing the dislocation of an ostium that is detected in the projection image by image analysis with respect to the position described in the vessel course information.

18. In a non-transitory computer-readable storage medium storing a program including instructions executable by a computer to determine stiffness information of a medical instrument used during an interventional procedure in a vascular system of a patient, the instructions comprising:
   recording a three-dimensional volume image of the vascular system at least in an intervention region;
   deriving from the three-dimensional volume image, three-dimensional vessel course information, the three-dimensional vessel course information comprising centerlines of at least vessels used by the medical instrument during the interventional procedure, surface information of at least the vessels used by the medical instrument during the interventional procedure, volume information of at least the vessels used by the medical instrument during the interventional procedure, a position of ostia along at least a part of the vessels, or any combination thereof;
   recording a two-dimensional projection image of the medical instrument using an x-ray device, wherein the x-ray device, the projection image, or the x-ray device and projection image are registered to the three-dimensional volume image; and
   determining the stiffness information of the medical instrument, the determining of the stiffness information of the medical instrument comprising evaluating the projection image using segmentation information determined by segmenting the instrument in the projection image, the vessel course information, or the projection image and the vessel course information.

19. The non-transitory computer-readable storage medium of claim 18, wherein when determining the stiffness information, at least one characteristic of the medical instrument is derived from the segmentation information;
   wherein a classification algorithm, a regression algorithm, or the classification algorithm and the regression algorithm evaluate the at least one characteristic to determine a stiffness class of the medical instrument;
   wherein each stiffness class is assigned a stiffness value used as the stiffness information.

20. The non-transitory computer-readable storage medium of claim 19, wherein determining the stiffness information further comprises determining the stiffness information using comparison information that is determined by comparing the course of the at least one vessel the instrument extends through according to the vessel course information and the course of the instrument according to the segmentation information; and
   wherein the classification algorithm, the regression algorithm, or the classification algorithm and the regression algorithm also evaluate the comparison information, ostium information, or comparison information and ostium information to determine the stiffness class.

* * * * *